United States Patent [19]

Shaposka et al.

[11] Patent Number: 4,753,697
[45] Date of Patent: Jun. 28, 1988

[54] TOTAL-CONTAINMENT STERILE PROCESS AND SYSTEM

[75] Inventors: John B. Shaposka; Dudley W. C. Spencer, both of Wilmington, Del.

[73] Assignee: Denco, Inc., Wilmington, Del.

[21] Appl. No.: 17,727

[22] Filed: Feb. 24, 1987

[51] Int. Cl.⁴ .................... A61M 5/00; B29C 65/20
[52] U.S. Cl. ..................... 156/158; 156/159; 156/304.2; 156/304.5; 156/304.6; 156/499; 156/503; 156/507; 604/905
[58] Field of Search .................. 156/158, 304.1, 304.2, 156/304.6, 502, 503, 507, 499, 159, 304.5; 604/283, 905

[56] References Cited

U.S. PATENT DOCUMENTS

| | | | |
|---|---|---|---|
| 3,013,925 | 12/1961 | Larson | 156/153 |
| 3,035,631 | 5/1962 | Knowles | 156/579 |
| 3,117,903 | 1/1964 | Hix | 156/158 |
| 3,769,124 | 10/1973 | Johnson | 156/159 |
| 3,834,971 | 9/1974 | Johnson | 156/507 |
| 3,897,296 | 7/1975 | Waldrum | 156/258 |
| 3,968,195 | 7/1976 | Bishop | 156/82 |
| 4,157,723 | 6/1979 | Granzow et al. | 141/1 |
| 4,209,013 | 6/1980 | Alexander | 128/213 A |
| 4,223,675 | 9/1980 | Williams | 604/410 |
| 4,242,310 | 12/1980 | Greff et al. | 312/1 |
| 4,253,500 | 3/1981 | Williams | 156/293 |
| 4,369,779 | 1/1983 | Spencer | 128/213 A |
| 4,405,312 | 9/1983 | Gross et al. | 604/29 |
| 4,412,835 | 11/1983 | Spencer | 604/29 |
| 4,443,215 | 4/1984 | Smith | 604/29 |
| 4,475,900 | 10/1984 | Popovich et al. | 604/29 |
| 4,507,119 | 3/1985 | Spencer | 604/280 |
| 4,516,971 | 5/1985 | Spencer | 156/304.2 |
| 4,521,263 | 6/1985 | Benen et al. | 156/159 |
| 4,610,670 | 9/1986 | Spencer | 604/29 |
| 4,619,642 | 10/1986 | Spencer | 604/29 |

OTHER PUBLICATIONS

*Transfusion*, "An Aseptic Fluid Transfer System for Blood and Blood Components", Sep.-Oct. 1978, pp. 546-552.

*Primary Examiner*—Michael Wityshyn
*Attorney, Agent, or Firm*—Connolly & Hutz

[57] ABSTRACT

A process and system is provided for making a connection between two fluid-filled plastic tubes that ensures total containment of potentially dangerous fluids and maintaining sterility of the connection. The tubes are folded to remove all fluid from the weld site and positioned to cause the connection to take place in this fluid free zone. Each folded section is first cauterized to create a bacteria free zone, the tubes are slit in the zone, and cauterized a second time to insure sterility and melt the tube ends. The tubes are urged together and as the thermoplastic resin cools, a totally contained, sterile weld is formed.

31 Claims, 5 Drawing Sheets

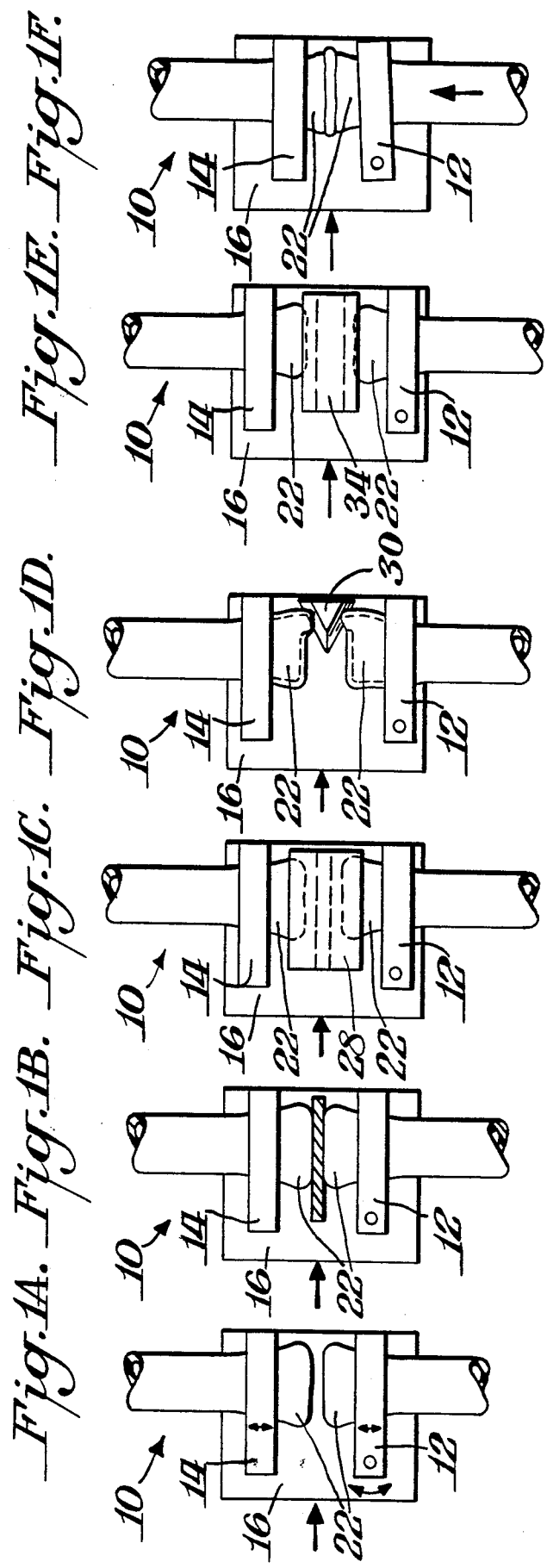

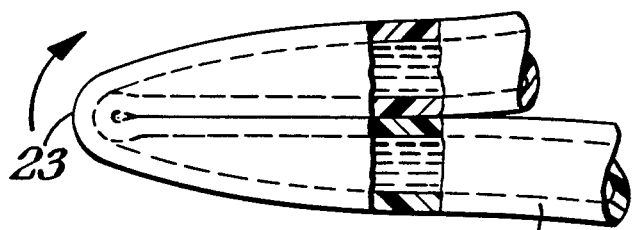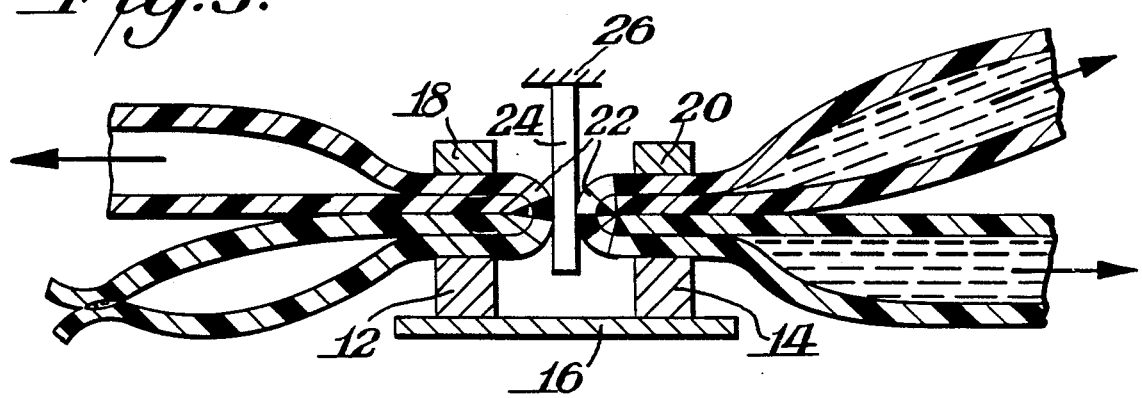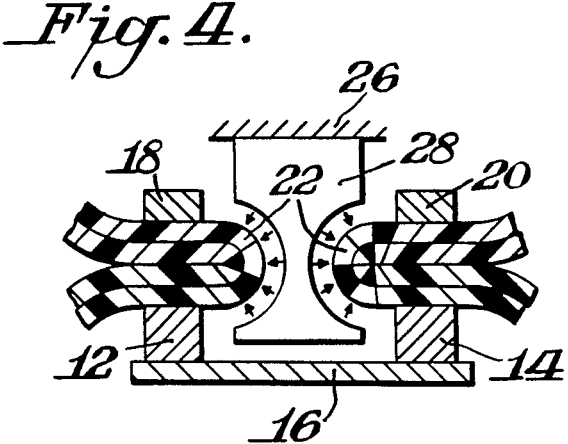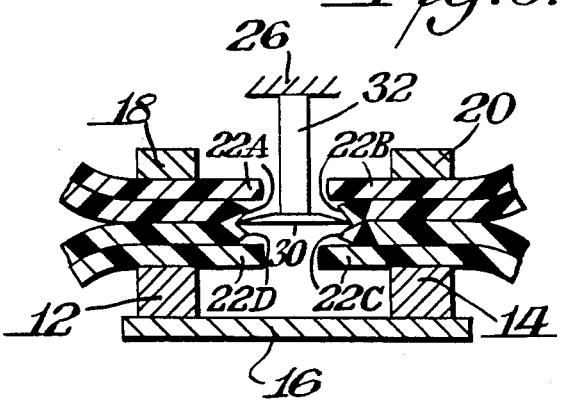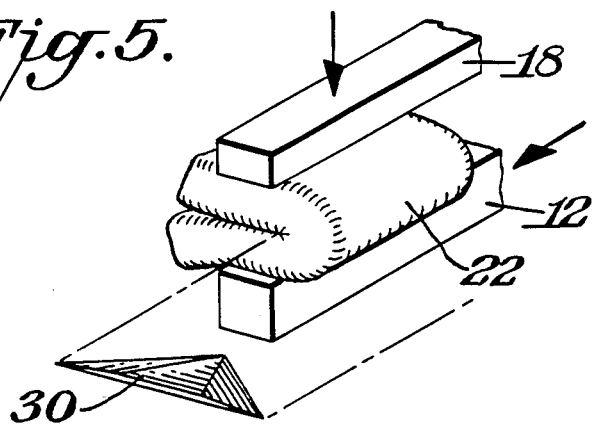

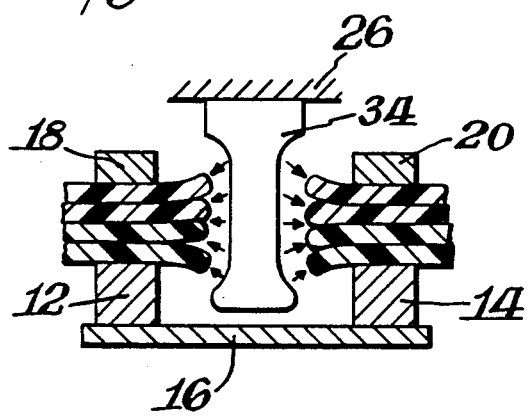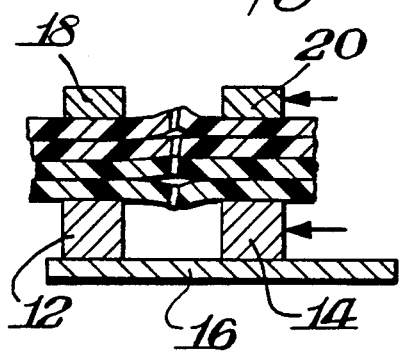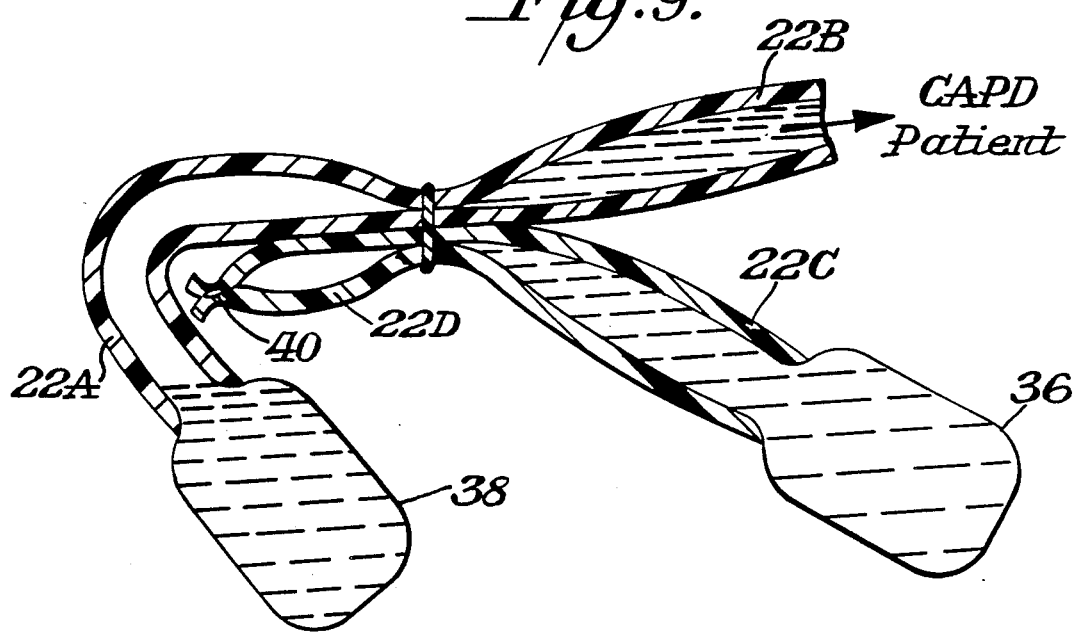

TOTAL-CONTAINMENT STERILE PROCESS AND SYSTEM

BACKGROUND OF INVENTION

This invention relates to a process and system for forming a total containment and sterile connection between two tubes.

At the present time, there are a number of medical and scientific procedures that require sterile transfer of dangerous or sensitive fluids from one container to another. This protects the internal fluids from external contamination. The fluids themselves, however, are frequently biologically or chemically dangerous. This is particularly true for medical personnel handling body fluids where AIDS, hepatitis or chemo-therapy agents are present. Total containment of the fluids therefore is important to protect patients and medical personnel from the dangers of infection from contact with the fluids.

An example of the need for a total containment, sterile system is in whole blood processing. Although great care is exercised to collect blood that is biologically clean, the organisms associated with AIDS and hepatitus are difficult to screen. Moreover, scientific work on the AIDS and hepatitus viruses require that the organism be present in the fluid samples. In either event the medical and scientific investigators are at high risk.

High risk areas associated with most body fluid handling are:
(a) Blood processing
(b) Bio-Medical technology Labs
(c) Dialysis, hemo and CAPD
(d) Total Parenteral feeding
(e) Chemo-therapy
(f) Urinary drainage (Post Operative)
(g) Indwelling catheters There is also a need for sterile connections for blood bags. At present, blood from a donor is drawn into a primary bag which may be joined to one or two satellite bags, all connected and sterilized before use. These satellite bags may be needed for holding blood separated components, such as plasma or platelets; treating agents, such as bases, buffers; stabilizers for cell metabolism, other preservatives, or rejuvenants; or washes to remove a treating agent or other contaminant. Actually, it is not feasible to have preconnected bags for all the treatments which may be desired. Supplemental treatment such as fresh preservative cannot now be added sterily during bag storage by any commercially acceptable procedure. In addition, to avoid the expense of unused satellite bags, the number of such bags is chosen based on limited, predicted needs. The inability to forecast needs well adds greatly to inventory requirements and complicates scheduling of blood donations.

Currently, very limited use is made of quality control as a time assay of the quantity and quality of components in separated blood fractions. The main reason for the current limited use is that heretofore any entry into a sterile blood unit exposed the blood to bacteria, thereby requiring that the blood be used within 24 hours from entry. Hence, although the viability of stored blood components can be extended by supplemental treatments, such treatments are usually not effective.

Moreover, the primary blood bag contains anticoagulant which can be sterilized only by heat (steam); thus all preconnected bags are also sterilized by wet-sterilization techniques, i.e., steam or hot water in an autoclave apparatus. These bags are also made of plasticized polyvinyl chloride (PVC), although other materials are known to be useful for constructing bags which are favorable for other reasons, such as greater oxygen permeability. Since many such materials, e.g., oxygen permeable polyethylene, are not steam sterilizable, they are not used in preconnected systems.

A sterile docking means would permit one to effect whatever processing is desired without compromising sterility, limiting storage life or requiring the preconnection of a multitude of bags, all wet-sterilizable, without knowing which, if any will be used.

In urinary drainage for example, it is important to ensure that no external organisms enter the system. The implanted catheter by-passes the body's immune defenses. Entry of bacteria into the system therefore can lead to bladder infections and possible life threatening bacteremia. The sterile connection feature of this invention safeguards this eventuality.

Hospital nurses also are at risk. The full bag of urine is exchanged by the nurse for an empty one. The full bag contents are weighed, and the urine disposed of. In this situation, it is extremely difficult to prevent urine from contacting the nurse's hands. A slight cut or opening contacted by AIDS or hepatitus organisms can lead to infection. The total containment features of this invention prevents this type of mishap.

Continuous ambulatory peritoneal dialysis (CAPD), is a procedure which replaces hemo-dialysis (a method of using membrane diffusion to wash the blood outside the body). The CAPD patient has a tube connected to his or her peritoneal cavity via an implanted catheter. A tube from a bag of fresh dialysis solution is connected to the patient's tube. The fresh dialysis solution is drained from the bag into the patient's peritoneal cavity where it remains for about 3-4 hours. During this treatment period, the empty bag is folded and carried by the patient who can continue with his or her normal activities. After this treatment period, the spent dialysate is drained back into the empty bag which is then disconnected from the patient's tube. A bag of fresh dialysis solution is then connected to the patient's tube and the procedure is repeated. Connection to a new bag of dialysis solution exposed the tube ends to airborne bacteria or other contamination even though precautions are taken. No satisfactory way heretofore has existed to insure sterility in spite of the elaborate and costly precautions now employed including the use of masks, gloves, gauze strips and disinfectant solutions. Usually, contamination does occur to the extent that a case of peritonitis is contracted perhaps on the average once or more a year and scar tissue from it inhibits dialysis.

Truly sterile connections could minimize the occurrence of peritonitis. Also any other treatment bags, such as for an antibiotic, bacteriostat, or other medications, could be connected as desired. The total containment capability of this patent provides for two further important features for CAPD.

The spent CAPD solution is totally contained in the spent bag and tube. This prevents accidental spillage or seepage of a fluid that could be biologically dangerous. Even if the patient accidentally reverses the tubes, he or she is still protected by the system remaining closed. The patient, recognizing the error, need only reload the same tubes and proceed to making the correct transfer.

A second advantage of the totally closed system is the ability to "bag-off". This is a situation where the patient does not wish to roll up the bag and tubing and wear it until the next exchange. While the dialysis solution is in the peritoneum the bag can be removed, thus the patients are free of a cumbersome and uncomfortable bulk under their clothing. The patient's life style is closer to normal. "Bagging-on" can also be a sterile-totally contained procedure.

U.S. Pat. Nos. 4,369,779 and 4,610,670 are generally directed to practices for such butt welding of plastic tubes. The various practices heretofore generally involve placing the two tubes to be welded in grooves in side by side holders. The holders move toward the heated wafer which in turn cuts through the tubes while also heating the tubes to their welding temperature. U.S. Pat. No. 4,619,642 discloses a variation of these practices wherein a cold cutting tool is used. A critical step in these practices involves the realignment of the tubes after the cutting process. This is accomplished by moving one of the holders with its cut tubes forwardly of the other holder so that a different pair of tube segments becomes aligned. The holders are then relatively moved toward each other to cause the realigned set of tubes to contact each other and become butt welded together. The result of this process is a pair of tube sections connected together and a second pair of tube sections unconnected to each other. The process has a number of disadvantages relating to the controls and consequently added expenditure resulting from the more complicated arrangement needed for the realigning step.

SUMMARY OF INVENTION

An object of this invention is to provide a butt welding assembly and process which avoids the disadvantages of the prior art.

A still further object of this invention is to provide such an assembly which results in two sets of tubes being totally contained and sterility butt welded together.

A further object of this invention is to provide such an assembly and process which is simpler in construction and use so as to lend itself to lower manufacturing cost and easier performance without sacrifice to effectiveness.

In accordance with this invention a key feature which lends itself to achieving the desired objects involves the step of folding each tube about a fold line. The tubes are then clamped in the folded condition after which the tubes are slit at the fold line to create two pairs of tube segments which are heated to their welding temperature and pressed into contact with each other without any realigning step and thereby resulting in two sets of butt welded tubes.

In a preferred practice of this invention the tubes are aligned with each other after being folded. Next the exposed surfaces of the folded tubes are subjected to radiant heat so as to become cauterized prior to slitting. Advantageously, the slitting may be accomplished by a cutting instrument at room temperature rather than requiring a heated wafer. The slitting tubes are then heated to their welding temperature prior to the butt welding step.

In an alternative form of this invention the heating and cutting takes place simultaneously by means of a heated wafer.

In addition to overcoming the above noted deficiencies of the prior art, there are several other important features associated with being able to achieve a totally contained-sterile weld. In the practice of the present invention, for example, the tubes are initially folded and the folding operation gently strips all of the fluid from the weld zone. This makes the weld area dry, but in addition, does not damage the internal fluids such as blood cells or nutrients. The weld area is a surface melting phenomena and not melting through the tube wall. This method of melting results in a weld stronger than the original tube with little or no internal occlusion.

Unlike systems mentioned in the prior art, this method of achieving total containment and a sterile weld need not require a consumable.

THE DRAWINGS

FIGS. 1A-1F are top plan views schematically showing the various stations in a butt welding assembly in accordance with this invention;

FIG. 2 is an elevation view partly in section showing the folding step for a tube in accordance with this invention;

FIG. 3 is a cross-sectional elevation view showing the aligning step corresponding to FIG. 1B;

FIG. 4 is a cross-sectional elevation view showing the cauterizing step corresponding to step 1C;

FIG. 5 is a perspective view showing the cauterized folded tube moving toward the slitting station.

FIG. 6 is a cross-sectional elevation view showing the tube slitting station corresponding to FIG. 1D.

FIG. 7 is a cross-sectional elevation view showing the heating station corresponding to FIG. 1E.

FIG. 8 is a cross-sectional elevation view showing the butt welding station corresponding to FIG. 1F.

FIG. 9 is a cross-sectional view showing two sets of butt welding tubes as used with a CAPD patient;

DETAILED DESCRIPTION

Figure 10:
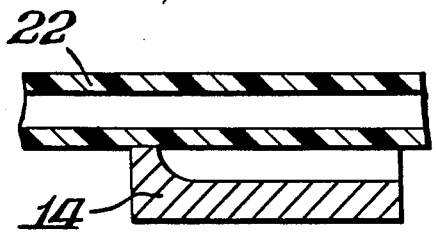
FIGS. 10-16 are cross-sectional elevation views showing the sequence of operation in an alternative practice of this invention.

FIGS. 1A-1F show a butt welding assembly 10 in accordance with this invention. As shown therein a pair of side by side holders 12, 14 are mounted on a support 16. Support 16 is movable back and forth in a horizontal direction through the various stations of the assembly. At least one of the holders, such as holder 14, is pivotally mounted so as to be movable toward and away from holder 12. Each holder 12, 14 also includes a clamp 18, 20 (FIGS. 3-8). Clamps 18 and 20 are aligned with each other and are preferably contoured to closely clamp the tubes in place of holders 12, 14. The details necessary for accomplishing these various movements may be of any suitable form known to those skilled in the art and may be based for example upon the structure disclosed in U.S. Pat. Nos. 4,369,779 and 4,610,670 and 4,619,642, the details of which are incorporated herein by reference thereto.

FIG. 2 illustrates the first step in the practice of this invention. As shown therein a tube 22 is folded so that the side of one tube portion contacts a side of the other tube portion. The fold generally takes place along the fold line 23. As illustrated the folding of the tube 22 results in cutting communication of the fluid in tube 22 with the folded portion near fold line 23 being free of fluid. A pair of such tubes 22 is placed in holders 12, 14 and by any suitable clamping device 18, 20 the tubes are mounted to holders 12, 14 until the welding is completed. The clamping operation preferably takes place when support 16 has been moved to the loading station of FIG. 1B.

At the loading station an alignment bar 24 is mounted for setting the proper spacing between the tubes 22 and assuring that the tubes are axially aligned with each other. FIG. 3 and FIG. 1B show the aligning station which includes an alignment bar 24 such as a plate mounted in any suitable manner such as from overhead rail 26 so that support 16 can pass under aligning bar 24. Where holders 12 and 14 are laterally movable, holders 12 and 14 are manipulated to move in a lateral direction unitl tubes 22, 22 contact aligning bar 24. Preferably, contoured clamps 18, 20 on holders 12, 14 may be opened sufficiently allowing the tubes 22, 22 to be axially moved until the tubes contact aligning bar 24. Clamps 18 and 20 would then be reengaged to firmly mount tubes 22, 22 their respective holders. In such case the tubes would be initially loaded while at aligning bar 24. Clamps 18, 20 may be of any suitable form such as having complementary grooves associated with grooves in holders 12, 14. The clamps may be closed in any suitable manners such by springs or threaded fasteners.

FIGS. 1C and 4 illustrate the next phase of operation wherein support 16 has moved to the cauterizing station. As illustrated in FIG. 4 a radiant heater 28 of any suitable construction is provided to apply heat to the exposed outer surfaces of tubes 22, 22. Heater 28 likewise is mounted in any suitable manner such as being suspended from rail 26. The distance established by aligning bar 24 is such that tubes 22, 22 are spaced the proper amount so that heater 28 fits between the tubes and is spaced from the tubes an appropriate distance to apply its radiant heat. Alternatively holders 12, 14 may be laterally moved toward or away from each other to accommodate heater 28 being between tubes 22, 22. The cauterizing step results in the creation of intense radiant heat for a brief period of time which is sufficient to kill any bacteria which may be clinging to the exterior of the tube walls.

FIG. 5 illustrates the next phase of operation wherein support 16 and the tube mounted holders are moved toward the slitting station which includes a cutting instrument 30 such as a knife or blade.

As shown in FIG. 1D and 6 (and FIG. 15), cutter 30 is positioned so that it cuts through the near wall of each tube and partially cuts the inner wall along their fold lines 23 to create four sets of individual tube sections 22A and 22D joined by a thin web and tube sections 22B and 22C also joined by their own web. In the preferred practice of this invention the slitting step is accomplished by a cold tool 30 which may for example be at room temperature. This represents a distinct departure from the prior art practice from using a heated wafer to cut through the tubes. As illustrated in FIG. 6 tool 30 may be mounted in any suitable manner, such as by securement to post 32 suspended from rail 26. When the tubes have been cut along their fold lines the relief of bending stresses in the tubes cause them to open up. If preferred cutting tool 30 may be initially heated to about 500° F. to assure that there is no surviving bacteria on the surface of tool 30.

As shown in FIGS. 1E and 7 the clamped tubes then move to a tube heating station which includes a further radiant heater 34 mounted in any suitable manner such as being suspended from rail 26. Heater 34 radiantly heats the exposed tube ends to their welding temperature.

As shown in FIGS. 1F and 8 the next station is the welding station where the four sets of tube ends 22A-D are pressed into contact with each other. This may be accomplished by any suitable means such as by pivoting holder 14 toward holder 12 as is known in the prior art. When the sets of tube ends are pressed together tube ends 22A and 22B become butt welded as do tube ends 22C and 22D.

After the butt welded sets of tubes have sufficiently cooled clamps 18, 20 are opened and the tubes are removed.

FIG. 9 illustrates a particular utility of the invention in connection with CAPD patients. As shown therein a bag 36 of used dialysate includes tube section 22C which has been folded over to form tube section 22B which in turn is connected to the patient. A bag 38 of new dialysate includes tube section 22A which had been folded over to include tube section 22D. Tube section 22C is sealed at remote stub end 40. The result of the slitting and butt welding operations is such that used bag 36 is then sealed at its end 40 since tube sections 22C and 22D become connected. Additionally, new bag 38 becomes in communication with the patient through tube sections 22A and 22B. The communication of the various tube sections is achieved by applying mechanical stress to the butt welding area so that the tubes become open and are restored to their initial round state.

The invention is particularly advantageous in that the desired tubes are welded together in a simple yet efficient manner. The stub end 40 of the new bag 38 becomes welded to the old bag 36 so that the contents of the old bag 36 are completely sealed. Similarly a sterile connection is made between the tube section 22B leading to the patient and the new bag 38. In this process a wafer is never contaminated with for example, molten PVC so there is no need to replace the wafer or cutting tool 30 between uses and therefore the cutting tool can be in effect permanent. By folding the tube in a manner described herein and clamping the tubes in their folded station no fluid remains in the weld area. Fluids which may easily be damaged (i.e. Blood) are gently removed from the weld area with this process. Moreover, the various cauterization or heating steps assure the elimination of any bacteria or spores in the weld area. A further advantage is that the folded tubes spontaneously open as the cutting tool passes through them because of the bending stresses. This prevents the cold cutting means from dragging bacteria into the lumen of the tubes. Further, the resultant welded tubes spontaneously open after removal from the clamps or, if so desired, may require the application of mechanical stress which can be achieved, for example, by a simple finger squeezing action. The two sets of welded tubes may be easily removed from each other by simply removing the tubes away from each other because the flashing between the tubes is sufficiently weak.

Tool 30 may be heated to about 500° F. and then the slitting may take place after tool 30 has cooled to room temperature (about 70° F.) or to an intermediate temperature, such as 320° F.

Figure 11:
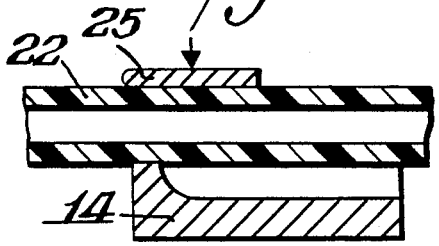
Figure 12:
Figure 13:
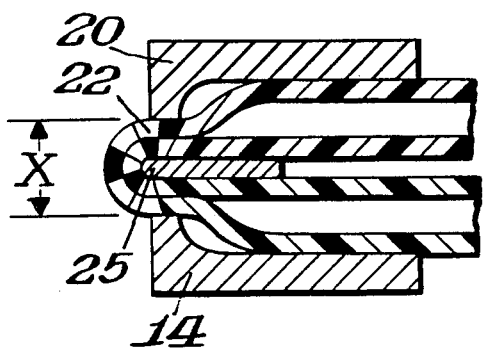
Figure 14:
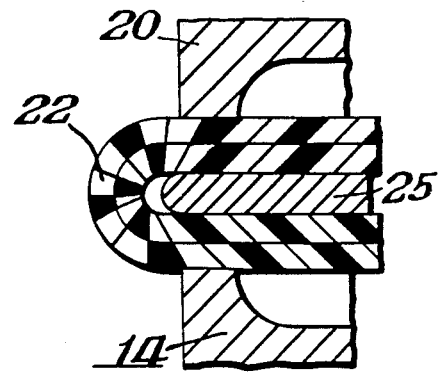
Figure 15:
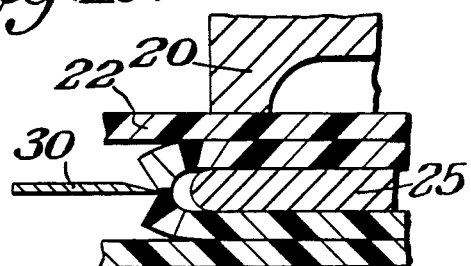
Figure 16:
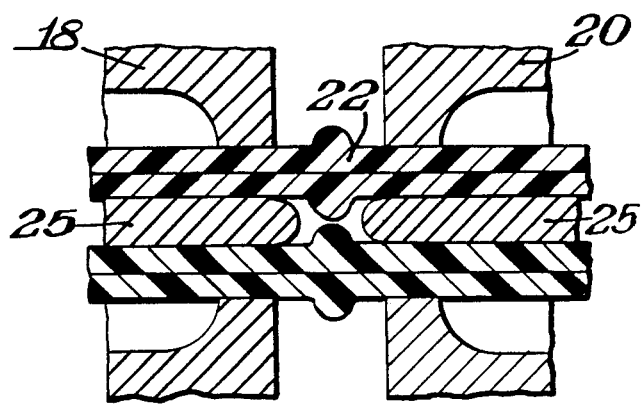

FIGS. 10-16 show a variation of the invention in which the folding of the tubes takes place about a locator bar. In this embodiment FIG. 10 illustrates the tube 22 being placed in the clamp base of holder 14. As shown in FIG. 11 plate-like locator bar 25 is then placed over tube 22 with its outer edge generally aligned with the outer edge of the base clamp. Tube 22 is next folded over locator bar 25 (FIG. 12) and clamp top 20 is secured in place (FIG. 13) to flatten tube 22 to the dimension "X" corresponding to the distance between the clamp base and top. FIG. 14 illustrates the flattened tube 22 prior to the slitting which is shown in FIG. 15. FIG. 15 also illustrates the slitting operation in which the near wall is completely slit but the inner wall is only partially cut leaving a thin web and resulting in the near wall bursting open because of the bending stress. FIG. 16 shows a second tube between the base clamp of holder 12 and upper clamp 18 with the two tubes butt welded together as previously described.

Advantageously locator bar 25 is pivotally connected to, for example, its respective clamp base so that it can conveniently swing into position after tube 22 is placed on the clamp base and then pivoted to its inactive position after the welding step.

Figure 17:
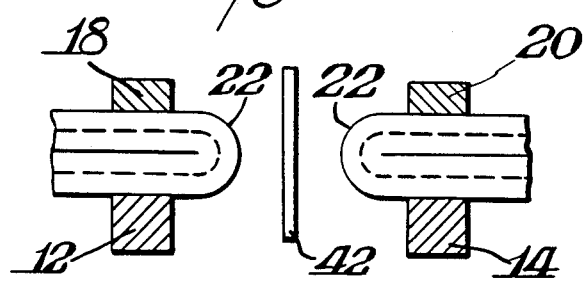
FIGS. 17-20 are cross-sectional elevation views showing the sequence of operations of yet a further alternative practice of this invention.

FIGS. 17–20 illustrate an alternative practice of this invention. In these Figures like reference numerals are used for like parts. As shown therein the folded tubes 22 are mounted in holders 12, 14 and maintained in their folded state by contoured clamps 18, 20, as in the prior arrangement. FIG. 17 however illustrates the use of a heated wafer 42 which may be of any suitable construction such as one of the forms illustrated and described in application Ser. No. 1955 filed Jan. 9, 1987, the details of which are incorporated herein by reference thereto.

Figure 18:
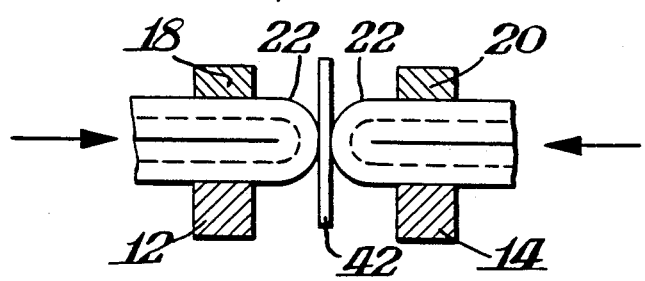
Figure 19:
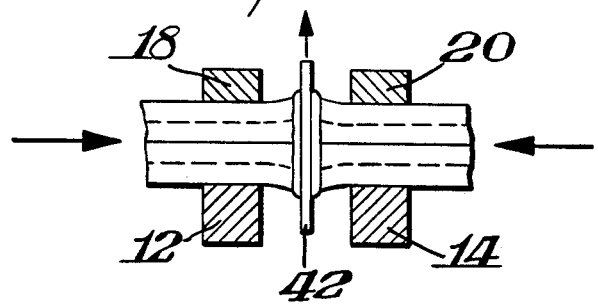

As shown in FIG. 18 the clamped tubes are moved laterally toward each other into contact with wafer 42. As the tubes approach the heating surface of wafer 42 the radiant heat kills any bacteria on the tube surface. Also since the wafer 42 or heating means is maintained at for example 425° F., contact with this wafer kills any surviving spores on the tube surface. FIG. 19 illustrates the heated wafer 12 cutting through the tubes with the tubes being heated to their welding temperature.

Figure 20:
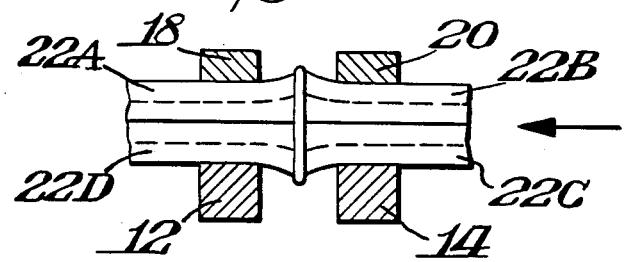

The wafer 42 is then slid from between the molten tube ends and, as shown in FIG. 20, the tubes are pressed together and butt welded. The tubes are allowed to cool in this state and then removed and reopened. As a result a weld is created between tube sections 22A and 22B and between tube sections 22C and 22D as previously described.

It is to be understood that the invention may be practiced in various manners without departing from the teachings herein. For example, in the broad practice of the invention the tubes need not be mounted to side by side jointly movable tube holders. Instead the tubes might be individually moved through their various stations. This practice of the invention however is not as desirable as the preferred practice since it would be more complicated.

A further alternative practice of the invention would be to mount the tubes to holders which remain at a fixed location and to move the various implements (such as heaters, cutter, etc.) to that fixed station in sequence. In such case the implements could be mounted to a movable rail either by being suspended from the rail or mounted on the rail whereupon the holders 12, 14 would have to have a slot therebetween to permit passage of the rail.

A still further alternative practice of the invention would be to sever the folded tips of the tubes using either a cold or hot cutting means. This would not be as desirable as the preferred embodiment since the severed tube tips would get into the mechanism causing possible jam-up of the drive mechanism.

What is claimed is:

1. A tube welding assembly for butt welding two plastic tubes together comprising a pair of holders, said holders being aligned with each other and being non-shiftable with respect to each other, each of said holders including clamping means for clamping a respective one of the tubes while the tube is transversely folded across a fold line, a slitting station having slitting means for being disposed between said holders, said holders and said slitting means being relatively movable with respect to each other to permit said slitting means to be positioned for slitting each of the folded tubes generally at their fold lines when the tubes are relatively moved into contact with said slitting means, a welding station having heating means, said holders and said heating means being relatively movable with respect to each other for heating the cut tubes to their welding temperature, and means for moving said holders toward each other to cause the heated cut tubes to contact each other and be butt welded together without any re-alignment of the tubes.

2. The assembly of claim 1 wherein said slitting means is unheated for cold slitting the tubes.

3. The assembly of claim 1 wherein said welding station is downstream from said slitting station.

4. The assembly of claim 3 wherein said holders are side by side holders spaced from each other.

5. The assembly of claim 1 wherein said holders are laterally movable toward and away from each other and are otherwise stationarily mounted, and said slitting station and said welding station being sequentially movable toward and away from said holders.

6. The assembly of claim 1 wherein said welding station further comprises a cauterizing station.

7. The assembly of claim 1 wherein said slitting means comprises a heated wafer, said wafer comprising said slitting means and said heating means, and said slitting station and said welding station being the same station.

8. The assembly of claim 1, in combination therewith, a first bag containing a first fluid, one of said tubes being connected to said first bag, a second bag containing a second fluid, and the other of said tubes being connected to said second bag.

9. The assembly of claim 8 wherein said first fluid is used dialysate, and said second fluid being fresh dialysate.

10. The assembly of claim 1, in combination with said plastic tubes, and each of said tubes being folded upon itself with the fold lines in line with each other.

11. A tube welding assembly for butt welding two plastic tubes together comprising a pair of holders, each of said holders including clamping means for clamping a respective one of the tubes while the tube is transversely folded across a fold line, a slitting station having slitting means for being disposed between said holders, said holders and said slitting means being relatively movable with respect to each other to permit said slitting means to be positioned for slitting each of the folded tubes generally at their fold lines when the tubes are relatively moved into contact with said slitting means, a welding station having heating means, said holders and said heating means being relatively movable with respect to each other for heating the cut tubes to their welding temperature, means for moving said holders toward each other to cause the heated cut tubes to contact each other and be butt welded together, an aligning station having an aligning member, said aligning member and said holders being relatively movable with respect to each other, and said aligning member being located in the spacing between said holders whereby the folded tubes may be aligned with each other against said aligning member.

12. The assembly of claim 11 including a cauterizing station upstream from said slitting station for heating the exposed outer surfaces of the folded tubes before the tubes are cut.

13. The assembly of claim 12 wherein each of said stations is stationary, and said holders being movable sequentially into each of said stations.

14. The assembly of claim 13 wherein said holders are jointly movable, and said means for moving said holders toward each other comprising pivot means on at least one of said holders.

15. The assembly of claim 14 wherein said clamping means comprises contoured clamps.

16. A tube welding assembly for butt welding two plastic tubes together comprising a pair of holders, each of said holders including clamping means for clamping a respective one of the tubes while the tube is transversely folded across a fold line, a slitting station having slitting means for being disposed between said holders, said holders and said slitting means being relatively movable with respect to each other to permit said slitting means to be positioned for slitting each of the folded tubes generally at their fold lines when the tubes are relatively moved into contact with said slitting means, a welding station having heating means, said holders and said heating means being relatively movable with respect to each other for heating the cut tubes to their welding temperature, means for moving said holders toward each other to cause the heated cut tubes to contact each other and be butt welded together, and a locator bar pivotally connected to each of said holders for being pivoted from a first inactive position to a second position whereby each tube may be folded over a respective locator bar.

17. A method of butt welding a pair of plastic tubes together comprising the steps of folding each tube along a fold line, clamping the tubes to maintain the tubes in a folded condition, slitting though each of the tubes generally along the fold line to form two sets of tube ends, heating the slit tubes to their welding temperature, and pressing the slit heated tubes together to butt weld at least one tube end from each of the tube sets together.

18. The method of claim 17 including permitting the tubes to cool after the tubes having been butt welded, and applying a mechanical force to the cooled butt welded tubes to cause the butt welded tubes to open and to be restored to their round shape.

19. The method of claim 17 wherein the slitting step is performed by an unheated slitting member.

20. The method of claim 19 including heating the exposed outer surfaces of the folded tubes in the area of the fold lines before the tubes are slit.

21. The method of claim 20 including moving the folded tubes toward an alignment bar until the fold lines contact the alignment bar before the tubes are heated and slit.

22. The method of claim 17 wherein the step of slitting the tubes is done with a heated wafer to simultaneously slit the tubes and heat the tubes to their welding temperature.

23. The method of claim 17 including moving the folded tubes toward an alignment bar until the fold lines contact the alignment bar before the tubes are slit.

24. The method of claim 17 wherein the folding step includes folding each tube over a locator bar, and permitting each locator bar to remain between its tube until after the butt welding step.

25. The method of claim 17 wherein the tool for slitting the tubes is heated to an elevated temperature and then permitted to cool before slitting.

26. The method of claim 25 wherein the cooling is to about room temperature.

27. The method of claim 25 wherein the cooling is to a temperature above room temperature.

28. The method of claim 17 wherein one of the tubes originally extends from a first bag and the other tube originally extends from a second bag, the butt welding resulting in the remote end of the one tube being mounted to the second bag and in the remote end of the other tube being mounted to the first bag.

29. The method of claim 28 wherein each bag contains a fluid, and stripping each set of butt welded tubes away from each other.

30. The method of claim 29 wherein each fluid is dialysate.

31. The method of claim 17 wherein after the tubes are slit the tube ends are pressed together without any realignment of the tube ends.

* * * * *